United States Patent
Zussman et al.

(10) Patent No.: US 9,950,093 B2
(45) Date of Patent: Apr. 24, 2018

(54) FIBER-REINFORCED HYDROGEL COMPOSITES AND METHODS OF FORMING FIBER-REINFORCED HYDROGEL COMPOSITES

(71) Applicants: Technion Research and Development Foundation Ltd, Haifa (IL); National University of Singapore, Singapore (SG)

(72) Inventors: Eyal Zussman, Haifa (IL); Srinivasa Reddy Chaganti, Haifa (IL); Jayarama Reddy Venugopal, Singapore (SG); Seeram Ramakrishna, Singapore (SG); Omri Regev, Haifa (IL)

(73) Assignees: National University of Singapore, Singapore (SG); Technion Research and Development Foundation LTD, Haifa (IL)

( * ) Notice: Subject to any disclaimer, the term of this patent is extended or adjusted under 35 U.S.C. 154(b) by 75 days.

(21) Appl. No.: 14/401,014

(22) PCT Filed: May 15, 2013

(86) PCT No.: PCT/SG2013/000196
§ 371 (c)(1),
(2) Date: Nov. 13, 2014

(87) PCT Pub. No.: WO2013/172788
PCT Pub. Date: Nov. 21, 2013

(65) Prior Publication Data
US 2015/0105863 A1   Apr. 16, 2015

Related U.S. Application Data

(60) Provisional application No. 61/647,166, filed on May 15, 2012.

(51) Int. Cl.
*A61F 2/02*   (2006.01)
*A61L 27/26*   (2006.01)
(Continued)

(52) U.S. Cl.
CPC ............... *A61L 27/26* (2013.01); *A61F 2/02* (2013.01); *A61L 27/48* (2013.01); *A61L 27/52* (2013.01);
(Continued)

(58) Field of Classification Search
CPC .......... A61L 27/26; A61L 27/38; A61L 27/48; A61L 27/52; A61F 2/02
See application file for complete search history.

(56) References Cited

U.S. PATENT DOCUMENTS 7,622,129 B1 * 11/2009 Haberstroh ............. A61L 27/18
424/400
8,187,621 B2 * 5/2012 Michal ................. A61K 9/0024
424/423
(Continued)

FOREIGN PATENT DOCUMENTS

WO    2007/001405 A2    1/2007
WO    2008/039530 A2    4/2008
(Continued)

OTHER PUBLICATIONS

Almany et al., "Biosynthetic hydrogel scaffolds made from fibrinogen and polyethylene glycol for 3D cell cultures," *Biomaterials* 26:2467-2477, 2005.
(Continued)

*Primary Examiner* — Victor Nguyen
(74) *Attorney, Agent, or Firm* — Seed Intellectual Property Law Group LLP

(57) ABSTRACT

A fiber-reinforced hydrogel composite is provided. The composite includes a hydrogel and a fibrous component
(Continued)

containing a plurality of fibers. Length of each of the plurality of fibers is less than about 1,000 μm. A method of preparing a fiber-reinforced hydrogel composite is also provided. The method includes coating a hydrogel precursor solution on a substrate to form a hydrogel precursor film, depositing the plurality of fibers onto the hydrogel precursor film, and allowing the hydrogel precursor film to form a hydrogel film, thereby forming the fiber-reinforced hydrogel composite. A scaffold containing the fiber-reinforced composite, and a tissue repair method using the fiber-reinforced composite are also provided.

16 Claims, 6 Drawing Sheets

(51) Int. Cl.
A61L 27/52 (2006.01)
A61L 27/48 (2006.01)
(52) U.S. Cl.
CPC ....... A61L 2400/06 (2013.01); A61L 2430/00 (2013.01); Y10T 428/31978 (2015.04)

(56) References Cited

U.S. PATENT DOCUMENTS

| 9,132,208 | B2* | 9/2015 | Chen | A61L 27/3604 |
|---|---|---|---|---|
| 2002/0114775 | A1* | 8/2002 | Pathak | A61K 9/0014 |
| | | | | 424/78.17 |
| 2007/0134333 | A1* | 6/2007 | Thomas | A61L 24/0031 |
| | | | | 424/486 |
| 2009/0074832 | A1 | 3/2009 | Zussman et al. | |

FOREIGN PATENT DOCUMENTS

| WO | 2009/042829 A1 | 4/2009 |
|---|---|---|
| WO | 2010/096795 A1 | 8/2010 |

OTHER PUBLICATIONS

Arinstein et al., "Buckling behaviour of electrospun microtubes: a simple theoretical model and experimental observations," *J. Phys. D: Appl. Phys.* 42:1-7, 2009.
Arinstein et al., "Postprocesses in tubular electrospun nanofibers," *Physical Review E* 76:056303-1-056303-7, 2007.
Banerjee et al., "Does the Anesthetic 2,2,2-Trifluoroethanol Interact with Bovine Serum Albumin by Direct Binding or by Solvent-Mediated Effects? A Calorimetric and Spectroscopic Investigation," *Biopolymers* 78:78-86, 2005.
Carrotta et al., "Protein stability modulated by a conformational effector: effects of trifluoroethanol on bovine serum albumin," *Phys. Chem. Chem. Phys.* 11:4007-4018, 2009.
Chu et al., "FTIR monitoring of oxazolidin-5-one formation and decomposition in a glycolaldehyde-phenylalanine model system by isotope labeling techniques," *Carbohydrate Research* 344:229-236, 2009.
Clasen et al., "The beads-on-string structure of viscoelastic threads," *J. Fluid Mech.* 556:283-308, 2006.
Coburn et al., "Biomimetics of the Extracellular Matrix: An Integrated Three-Dimensional Fiber-Hydrogel Composite for Cartilage Tissue Engineering," *Smart Struct Syst.* 7(3):213-222, Jan. 2011.
Draye et al., "In vitro and in vivo biocompatibility of dextran dialdehyde cross-linked gelatin hydrogel films," *Biomaterials* 19:1677-1687, 1998.
Draye et al., "In vitro release characteristics of bioactive molecules from dextran dialdehyde cross-linked gelatin hydrogel films," *Biomaterials* 19:99-107, 1998.
Dror et al., "Nanofibers Made of Globular Proteins," *Biomacromolecules* 9(10):2749-2754, 2008.

Drury et al., "Hydrogels for tissue engineering: scaffold design variables and applications," *Biomaterials* 24:4337-4351, 2003.
Ekaputra et al., "Combining Electrospun Scaffolds with Electrosprayed Hydrogels Leads to Three-Dimensional Cellularization of Hybrid Constructs," *Biomacromolecules* 9(8):2097-2103, 2008.
Eyrich et al., "Long-term stable fibrin gels for cartilage engineering," *Biomaterials* 28:55-65, 2007.
Feingold-Leitman et al., "In Vitro Evaluation of a Composite Scaffold Made from Electrospun Nanofibers and a Hydrogel for Tissue Engineering," *Journal of Bionanoscience* 3(1):1-13, 2009.
Ghosh et al., "Cell adaptation to a physiologically relevant ECM mimic with different viscoelastic properties," *Biomaterials* 28:671-679, 2007.
Greenfeld et al., "Polymer dynamics in semidilute solution during electrospinning: A simple model and experimental observations," *Physical Review E* 84:041806-1-041806-9, 2011.
Hayami et al., "Design and characterization of a biodegradable composite scaffold for ligament tissue engineering," *Journal of Biomedical Materials Research Part A*:1407-1420, 2009.
Hersel et al., "RGD modified polymers: biomaterials for stimulated cell adhesion and beyond," *Biomaterials* 24:4385-4415, 2003.
Hoffman, "Hydrogels for biomedical applications," *Advanced Drug Delivery Reviews* 54:3-12, 2002.
Hsieh et al., "Hydrogel/electrospun fiber composites influence neural stem/progenitor cell fate," *Soft Matter* 6:2227-2237, 2010.
Kundu et al., "Interaction of 2, 2, 2-trifluoroethanol with proteins: calorimetric, densimetric and surface tension approach," *Biophysical Chemistry* 109:427-442, 2004.
Landa et al., "Effect of Injectable Alginate Implant on Cardiac Remodeling and Function After Recent and Old Infarcts in Rat," *Circulation* 117:1388-1396, 2008.
Lewus, "In Vitro Characterization of a Bone Marrow Stem Cell-Seeded Collagen Gel Composite for Soft Tissue Grafts: Effects of Fiber Number and Serum Concentration," *Tissue Engineering* 11(7/8):1015-1022, 2005.
Moutos et al., "Multifunctional Hybrid Three-dimensionally Woven Scaffolds for Cartilage Tissue Engineering," *Macromol. Biosci.* 10:1355-1364, 2010.
Nguyen et al., "Injectable Biodegradable Hydrogels," *Macromol. Biosci.* 10:563-579, 2010.
Qin, "The Preparation and Characterization of Fiber Reinforced Alginate Hydrogel," *Journal of Applied Polymer Science* 108:2756-2761, 2008.
Qu, "Novel pH-sensitive chitosan hydrogels: swelling behavior and states of water," *Polymer* 41:4589-4598, 2000.
Regev et al., "About the albumin structure in solution and related electro-spinnability issues," *International Journal of Biological Macromolecules* 47:261-265, 2010.
Regev et al., "The role of interfacial viscoelasticity in the stabilization of an electrospun jet," *Polymer* 51:2611-2620, 2010.
Reneker et al., "Electrospinning of Nanofibers from Polymer Solutions and Melts," *Advances in applied mechanics* 41:43-197, 2007.
Rosenblatt et al., "Injectable collagen as a pH-sensitive hydrogel," *Biomaterials* 15(12):985-995, 1994.
Ross-Murphy, "Structure and rheology of gelatin gels: recent progress," *Polymer* 33(12):2622-2627, 1992.
Schacht et al., "Hydrogels prepared by crosslinking of gelatin with dextran dialdehyde," *Reactive & Functional Polymers* 33:109-116, 1997.
Schacht et al., "Some Aspects of the Crosslinking of Gelatin by Dextran Dialdehydes," *Polymer Gels and Networks* 1:213-224, 1993.
Schnitzer et al., "Albondin-mediated Capillary Permeability to Albumin: Differential Role of Receptors in Endothelial Transcytosis and Endocytosis of Native and Modified Albumins," *The Journal of Biological Chemistry* 269(8):6072-6082, Feb. 1994.
Slivka et al., "Porous, Resorbable, Fiber-Reinforced Scaffolds Tailored for Articular Cartilage Repair," *Tissue Engineering* 7(6):767-780, 2001.
Storm et al., "Nonlinear elasticity in biological gels," *Nature* 435:191-194, May 2005.

(56) References Cited

OTHER PUBLICATIONS

Tan et al., "Injectable in situ forming biodegradable chitosan-hyaluronic acid based hydrogels for cartilage tissue engineering," *Biomaterials* 30:2499-2506, 2009.

Tan et al., "Injectable, Biodegradable Hydrogels for Tissue Engineering Applications," *Materials* 3:1746-1767, 2010.

Tan et al., "Thermosensitive injectable hyaluronic acid hydrogel for adipose tissue engineering," *Biomaterials* 30:6844-6853, 2009.

Tibbit et al., "Hydrogels as Extracellular Matrix Mimics for 3D Cell Culture," *Biotechnol. Bioeng.* 103:655-663, Jul. 2009.

Tiwari et al., "Optimizing partition-controlled drug release from electrospun core-shell fibers," *International Journal of Pharmaceutics* 392:209-217, 2010.

Vanderhooft et al., "Rheological Properties of Cross-Linked Hyaluronan-Gelatin Hydrogels for Tissue Engineering," *Macromol. Biosci.* 9:20-28, 2009.

Xu et al., "Material properties and osteogenic differentiation of marrow stromal cells on fiber-reinforced laminated hydrogel nanocomposites," *Acta Biomaterialia* 6:1992-2002, 2010.

Zhao et al., "A polylactide/fibrin gel composite scaffold for cartilage tissue engineering: fabrication and an in vitro evaluation," *J. Mater. Sci.: Mater. Med.* 20:135-143, 2009.

Zhong et al., "Formation of Collagen-Glycosaminoglycan Blended Nanofibrous Scaffolds and Their Biological Properties," *Biomacromolecules* 6(6):2998-3004, 2005.

Zussman et al., "Failure modes of electrospun nanofibers," *Applied Physics Letters* 82(22):3958-3960, Jun. 2003.

\* cited by examiner (i) gelatin
(ii) dextran
(iii) albumin
(iv) cells dextran−C=N−gelatin (with H above C)

ABRIC-REINFORCED HYDROGEL
COMPOSITES AND METHODS OF
FORMING FIBER-REINFORCED
HYDROGEL COMPOSITES

CROSS-REFERENCE TO RELATED APPLICATION

This application claims the benefit of priority of U.S. provisional application No. 61/647,166 filed on 15 May 2012, the content of which is incorporated herein by reference in its entirety for all purposes.

TECHNICAL FIELD

The invention relates to hydrogels, more particularly, to fiber-reinforced hydrogel composites, and methods of forming the fiber-reinforced hydrogel composites.

BACKGROUND

Hydrogels are primarily composed of synthetic or natural hydrophilic polymers. Owing to their 3-D structures, which resemble that of extracellular matrices (ECMs), hydrogels have been employed as tissue substitutes, space-filling scaffolds, and cell carriers. To achieve maximal benefit, the hydrogel composition must be compatible with the mechanical (for example, modulus), physical (for example, mass transport) and biological (for example, cell-matrix interaction) requirements of each biomedical application under consideration. In particular, injectable hydrogels as biomaterials are attractive for many biomedical applications.

Strength of hydrogels depends largely on their cross-link density, which may be physical (reversible) or chemical (permanent) in nature. Physical networks may be present in hydrogels such as collagen, chitosan, and aminated hyaluronic acid (HA)-g-poly(N-isopropylacrylamide), whereas chemical networks may be found in chitosan-HA, polyethylene glycol-fibrinogen, and alginate hydrogels. However, such systems are usually weak isotropic materials and are not able to bear significant loads, such as those presented by living tissues, and also suffer from poor stability and survival following engraftment.

Fiber reinforcement may be used to strengthen hydrogels and to obtain composite structures featuring anisotropic mechanical behavior. Supportive impact of hydrogel/electrospun fiber composites on cell growth and differentiation has been reported. However, incorporation of fibers and their proper dispersion within the host material still pose a technological challenge, especially in case of injectable hydrogels, where injectability is required and blockage of needles must be avoided.

In view of the above, there remains a need for hydrogel compositions, and methods of forming the hydrogel compositions that address at least one of the above-mentioned problems.

SUMMARY

In a first aspect, the invention refers to a fiber-reinforced hydrogel composite comprising: a hydrogel; and a fibrous component comprising a plurality of fibers, wherein the length of each of the plurality of fibers is less than about 1,000 µm.

In a second aspect, the invention refers to a method of preparing a fiber-reinforced hydrogel composite according to the first aspect, the method comprising: coating a hydrogel precursor solution on a substrate to form a hydrogel precursor film; depositing the plurality of fibers onto the hydrogel precursor film; and allowing the hydrogel precursor film to form a hydrogel film, thereby forming the fiber-reinforced hydrogel composite.

In a third aspect, the invention refers to a scaffold comprising the fiber-reinforced hydrogel composite according to the first aspect.

In a fourth aspect, the invention refers to a tissue repair method, the method comprising contacting the tissue with a scaffold according to the third aspect.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
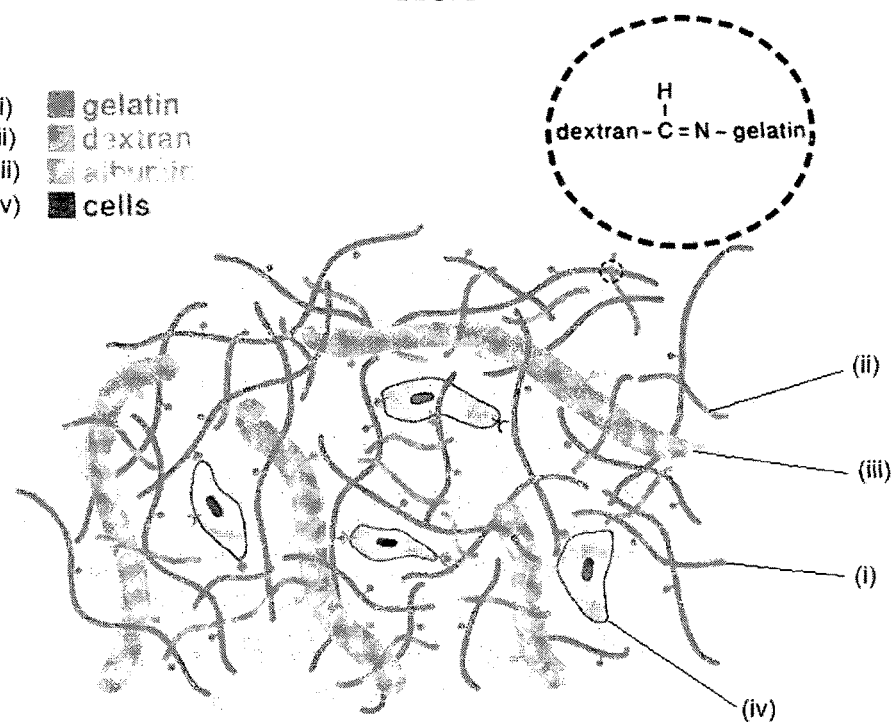
FIG. 1 shows a schematic diagram of the tested hybrid biomaterial having (i) gelatin, (ii) dextran, (iii) albumin, and (iv) cells according to an embodiment. The inset shows the covalent bond between the aldehyde group of modified dextran and the amino group of gelatin.

By embedding short-length fibers, wherein length of each fiber is less than about 1,000 μm, in a hydrogel, properties of the resultant composite may be improved due to structural reinforcement of the hydrogel by the fibers. In various embodiments, for example, elastic modulus of the hydrogel component in the composite is increased by about 40% and gelation time for the hydrogel is decreased by about 20%. This may be attributed to the short length of the reinforcing fibers, which facilitate dispersion of the fibers within the hydrogel and injectability of the resultant composite. The hydrogel, on the other hand, retains its properties as a tunable matrix for various applications. For example, injection performance of the pre-gel solution through medical needles at moderate shear rates is not affected by presence of the short-length fibers in the composite. Viability of seeded fibroblasts in experiments conducted has confirmed the biocompatibility of scaffolds formed using a fiber-reinforced hydrogel composite according to various embodiments of the invention. This fiber-reinforced hydrogel composite material represents a class of biomaterials that structurally mimics the extracellular matrices (ECMs) of common tissues, and may be delivered by a minimal invasive approach.

Accordingly, in a first aspect, the present invention relates to a fiber-reinforced hydrogel composite. The term "composite" as used herein refers to a construct including a fibrous component and a hydrogel component. The components in the composite may be physically mixed together to form the composite. By the term "physically mixed", it is meant that the hydrogel component and the fibrous component are merely dispersed in one another, and do not chemically react to form a new material.

The fibrous component comprises a plurality of fibers. The term "fiber" as used herein refers to a class of materials, that may be natural or synthetic, that are in discrete elongated pieces. They may be used as a component of composite materials, or matted into sheets. They may further be used in the manufacturing of composites via cross-linking, gluing, weaving, braiding, knitting, knotting, molding, and the like.

The fibers may be produced by conventional techniques such as electrospinning, interfacial polymerization, and the like. Electrospinning affords control of the length of the resultant electrospun fibers by, for example, varying the voltage applied to the needle or by varying the composition of the melt or solution in the syringe. Thus, in various embodiments, the plurality of fibers consists of electrospun fibers, wherein the fibers are produced by electrospinning.

In electrospinning, fibers are formed by application of an electrical charge on a liquid to draw micro- or nano-fibers from the liquid. The process may comprise the use of a spinneret with a dispensing needle, a syringe pump, a power supply and a grounded collection device. Material to form the fibers may be present as a melt or a spinning solution in the syringe, and driven to the needle tip by the syringe pump where they form a droplet. When voltage is applied to the needle, a droplet is stretched to an electrified liquid jet. The jet is elongated continuously until it is deposited on the collector as a mat of fine fibers of micrometer or nanometer sized dimensions.

In this regard, it has been surprisingly found by the inventors of the present invention that use of a solution that does not contain water, for example, a non-aqueous solution, or a solution that is essentially free of water as the spinning solution results in short-length fibers with each fiber having a length of less than about 1,000 μm. By the term "essentially free", it is meant that the solution contains less than 1 wt % water, such as less than 0.5 wt %, less than 0.3 wt %, or less than 0.1 wt % water. As mentioned above, the short-length fibers which are produced may be dispersed readily into a hydrogel to form a fiber-reinforced hydrogel composite. In so doing, the short-length fibers reinforce structure of the hydrogel to result in improved physical properties of the hydrogel, such as increase in elastic modulus and decrease in gelation time, while maintaining injectability of the hydrogel.

In various embodiments, the composite consists of less than about 10 wt % of the fibrous component based on the total weight of the composite. For example, the composite may consist of about 1 wt % to about 6 wt % of the fibrous component based on the total weight of the composite, such as about 1 wt % to about 5 wt %, about 1 wt % to about 4 wt %, about 1 wt % to about 3 wt %, about 2 wt % to about 6 wt %, about 2 wt % to about 5 wt %, about 2 wt % to about 4 wt %, about 3 wt % to about 6 wt %, about 3 wt % to about 5 wt %, or about 1 wt %, about 2 wt %, about 3 wt %, about 4 wt %, about 5 wt %, or about 6 wt %.

The plurality of fibers may be selected from the group consisting of fibers that comprise or consist of proteins, carbohydrates, hydroxy carboxylic acids, or combinations thereof. In such embodiments, the fibers may comprise or consist of albumin, collagen, elastin, alginate, polylactide, polyamide, poly(siloxane), poly(silicone), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polyglycolide, poly(lactide-co-glycolide), polyanhydride, polyorthoester, poly(carbonate), poly(ethylene oxide), polyaniline, poly(vinyl phenol), polyhydroxyacid, poly(caprolactone), polyhydroxyalkanoate, polyurethane, chitosan, starch, hyaluronic acid, blends thereof, or copolymers thereof.

In various embodiments, the fibers consist of serum albumin. For example, the fibers may consist of bovine serum albumin.

The fiber-reinforced hydrogel composite according to the first aspect comprises a fibrous component, the fibrous component comprising a plurality of fibers, wherein the length of each of the plurality of fibers is less than about 1,000 μm. Fibers of this (short) length range facilitate dispersion of the fibers within the hydrogel while retaining injectability of the resultant composite.

In various embodiments, the length of each of the plurality of fibers is about 100 μm to about 1,000 μm, such as about 100 μm to about 800 μm, about 100 μm to about 500 μm, about 100 μm to about 300 μm, about 300 μm to about 1,000 μm, about 500 μm to about 1,000 μm, about 800 μm to about 1,000 μm, about 300 μm to about 800 μm, about 300 μm to about 500 μm, or about 500 μm to about 800 μm.

The aspect ratio, defined herein as ratio of length to width of each fiber, is typically about 100:1. The width of each of the plurality of fibers is generally less than about 5 µm, such as about 2 µm to about 5 µm, about 1 µm to about 3 µm, about 2 µm to about 3 µm, about 0.5 µm to about 3 µm, about 1 µm, about 2 µm, about 3 µm, about 4 µm, or about 5 µm. In various embodiments, the width of each of the plurality of fibers is about 2 µm.

Besides the fibrous component, the fiber-reinforced hydrogel composite also comprise a hydrogel. The term "hydrogel" as used herein refers to a broad class of polymeric materials, that may be natural or synthetic, which have an affinity for an aqueous medium, and is able to absorb large amounts of the aqueous medium, but which do not normally dissolve in the aqueous medium.

The term "aqueous medium" as used herein refers to water or a solution based primarily on water such as phosphate-buffered saline (PBS), or water containing a salt dissolved therein. The term "aqueous medium" may also refer to a cell culture medium. The term "cell culture medium" may also be termed as a "growth medium", and refers to any liquid medium which enables cells proliferation. Growth media are known in the art and may be selected depending on the type of cells to be grown. For example, a growth medium suitable for use in growing mammalian cells is Dulbecco's Modified Eagle Medium (DMEM), which may be supplemented with heat inactivated fetal bovine serum and embryonic stem cells derived conditioned medium.

A hydrogel is characterized by a high permeability for exchange of nutrients necessary for cell proliferation. The physical properties of hydrogels are similar to native tissue, and hydrogels may be used to encapsulate cells in the hydrogel matrix formed upon gelation. In various embodiments, an injectable hydrogel, which may be injected into a subject of interest, is used.

Generally, a hydrogel may be formed by using at least one, or one or more types of hydrogel precursor, and setting or solidifying the one or more types of hydrogel precursor in an aqueous solution to form a three-dimensional network, wherein formation of the three-dimensional network may cause the one or more types of hydrogel precursor to gel.

The term "hydrogel precursor" refers to any chemical compound that may be used to form a hydrogel. Examples of hydrogel precursors include, but are not limited to, a natural polymer, a hydrophilic monomer, a hydrophilic polymer, a hydrophilic copolymer formed from a monomer and a polymer.

In various embodiments, the hydrogel precursor comprises or consists of a natural polymer. The natural polymer may form a three-dimensional network in an aqueous medium to form a hydrogel. A "natural polymer" refers a polymeric material that may be found in nature. Examples of a natural polymer include, but are not limited to, polysaccharide, glycosaminoglycan, protein, peptide and polypeptide.

Polysaccharides are carbohydrates which may be hydrolyzed to two or more monosaccharide molecules. They may contain a backbone of repeating carbohydrate i.e. sugar unit. Examples of polysaccharides include, but are not limited to, alginate, agarose, chitosan, dextran, starch, and gellan gum.

Glycosaminoglycans are polysaccharides containing amino sugars as a component. Examples of glycosaminoglycans include, but are not limited to, hyaluronic acid, chondroitin sulfate, dermatin sulfate, keratin sulfate, dextran sulfate, heparin sulfate, heparin, glucuronic acid, iduronic acid, galactose, galactosamine, and glucosamine.

Peptides refer generally to amino acid dimers (dipeptides), oligomers (oligopeptides) of up to about 25 to 50 amino acids, and short polymers of about 2 to 100 amino acids in length. Polypeptide refers generally to a single chain amino acid polymer of more than 100 amino acid monomers. Protein refers generally to a 3D-structure of one or more polypeptide chains that may be non-covalently or covalently (via disulfide bridges) be associated with each other. Proteins have diverse biological functions and may be classified into five major categories, i.e. structural proteins such as collagen, catalytic proteins such as enzymes, transport proteins such as hemoglobin, regulatory proteins such as hormones, and protective proteins such as antibodies and thrombin. Other examples of proteins include, but are not limited to, gelatin, fibronectin, fibrin, pectins, albumin, ovalbumin, and polyamino acids.

In some embodiments, the hydrogel precursor comprises or consists of a hydrophilic monomer. As used herein, a hydrophilic monomer refers to any monomer which, when polymerized, yields a hydrophilic polymer capable of forming a hydrogel when contacted with an aqueous medium such as water. In some embodiments, a hydrophilic monomer may contain a functional group in the polymer backbone or as lateral chains. The term "functional group" as used herein refers to a chemical moiety which exhibits bond formation capability. Examples of functional group include, but are not limited to, hydroxyl (—OH), carboxyl (—COOH), amide (—CONH—), thiol (—SH), or sulfonic (—SO$_3$H) groups.

Examples of hydrophilic monomers include, but are not limited to, hydroxyl-containing monomers such as 2-hydroxyethyl methacrylate, 2-hydroxyethyl acrylate, 2-hydroxyethyl methacrylamide, 2-hydroxyethyl acrylamide, N-2-hydroxyethyl vinyl carbamate, 2-hydroxyethyl vinyl carbonate, 2-hydroxypropyl methacrylate, hydroxyhexyl methacrylate and hydroxyoctyl methacrylate; carboxyl-containing monomers such as acrylic acid, methacrylic acid, itaconic acid, fumaric acid, crotonic acid, maleic acid and salts thereof, esters containing free carboxyl groups of unsaturated polycarboxylic acids, such as monomethyl maleate ester, monoethyl maleate ester, monomethyl fumarate ester, monoethyl fumarate ester and salts thereof; amide containing monomers such as (meth)acrylamide, crotonic amide, cinnamic amide, maleic diamide and fumaric diamide; thiol-containing monomers such as methanethiole, ethanethiol, 1-propanethiol, butanethiol, tert-butyl mercaptan, and pentanethiols; sulfonic acid-containing monomers such as p-styrenesulfonic acid, vinylsulfonic acid, p-a-methylstyrene sulfonic acid, isoprene sulfonide and salts thereof.

In some embodiments, the hydrogel precursor comprises or consists of a hydrophilic polymer. The hydrophilic polymer may be a polymer that is made up of any one of the above mentioned hydrophilic monomer, and which may be formed from any reaction such as, but not limited to, free radical polymerization, condensation polymerization, anionic or cationic polymerization, or step growth polymerization. For example, a hydrophilic monomer such as ethylene glycol may undergo anionic or cationic polymerization, depending on the type of catalyst used, to form poly(ethylene glycol) which is a hydrophilic polymer. The hydrophilic polymer may also be obtained by chemical modification of an existing polymer. For example, a functional group may be added or altered on polymeric chains such that the resultant polymer is made hydrophilic.

In some embodiments, the hydrogel precursor comprises or consists of a hydrophilic copolymer. The hydrophilic copolymer may be formed from a hydrophilic polymer and a monomer which may be hydrophilic, hydrophobic or amphiphilic. In some embodiments, a hydrophilic copolymer may be formed from a hydrophilic monomer and a polymer which may be hydrophilic, hydrophobic or amphiphilic. For example, a hydrophobic monomer may react with a functional group present on a hydrophilic polymer to form a hydrophilic copolymer.

The one of more types of hydrogel precursors may set or solidify in an aqueous medium to form a three-dimensional network, wherein formation of the three-dimensional network can cause the one or more types of hydrogel precursor to gel. For example, a hydrogel may be formed by physical bonding such as self assembly, or chemical bonding such as cross-linking, of one or more types of hydrogel precursors in an aqueous medium.

In some embodiments, a hydrogel may be formed by self-assembly of one or more types of hydrogel precursors in an aqueous medium. The term "self-assembly" refers to a process of spontaneous organization of components of a higher order structure by reliance on the attraction of the components for each other, and without chemical bond formation between the components. For example, polymer chains may interact with each other via any one of hydrophobic forces, hydrogen bonding, Van der Waals interaction, electrostatic forces, or polymer chain entanglement, induced on the polymer chains, such that the polymer chains may aggregate or coagulate in an aqueous medium, which may form a three-dimensional network, thereby entrapping molecules of water to form a hydrogel.

In some embodiments, a hydrogel may be formed by chemical bonding between one or more types of hydrogel precursors in an aqueous medium. For, example, when the hydrogel precursor is a hydrophilic polymer, the polymeric chains may be cross-linked using a suitable cross-linking agent to form a three-dimensional network, which may entrap water molecules to form a hydrogel.

The term "cross-link" as used herein refers to an interconnection between polymer chains via chemical bonding, such as, but not limited to, covalent bonding, ionic bonding, or affinity interactions (e.g. ligand/receptor interactions, antibody/antigen interactions, etc.). The chemical cross-linking may be carried out by reactions, such as any one of free radical polymerization, condensation polymerization, anionic or cationic polymerization, or step growth polymerization.

The term "cross-linking agent" refers to an agent which induces cross-linking. The cross-linking agent may be any agent that is capable of inducing a chemical bond between adjacent polymeric chains. For example, the cross-linking agent may be a chemical compound. Examples of chemical compounds that may act as cross-linking agent include, but are not limited to, dextran dialdehyde, 1-ethyl-3-[3-dimethylaminopropyl]carbodiimide hydrochloride (EDC), vinylamine, 2-aminoethyl methacrylate, 3-aminopropyl methacrylamide, ethylene diamine, ethylene glycol dimethacrylate, methymethacrylate, N,N'-methylene-bisacrylamide, N,N'-methylenebis-methacrylamide, diallyltartardiamide, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth) acrylate, methylenebis(meth)acrylamide, triallyl phthalate, diallyl phthalate, transglutaminase, or mixtures thereof.

In various embodiments, the cross-linking agent comprises or consists of dextran dialdehyde. When dextran dialdehyde is added to a hydrogel precursor such as gelatin, for example, covalent bonds such as that shown in the inset of FIG. 1 is formed between the aldehyde group of the dextran dialdehyde and the amino group of gelatin, thereby cross-linking the gelatin to form dextran dialdehyde-cross-linked gelatin hydrogel via chemical bonding.

In some embodiments, the hydrogel precursors may themselves be used as cross-linking agents, and do not require addition or use of a separate cross-linking agent.

In some embodiments, the cross-linking agent may be in the form of an electromagnetic wave. Therefore, cross-linking may be carried out using an electromagnetic wave, such as gamma or ultraviolet radiation, which may cause the polymeric chains to cross-link and form a three-dimensional matrix, thereby entrapping water molecules to form a hydrogel. Therefore, choice of cross-linking agent is dependent on the type of polymeric chain and functional group present, and a person skilled in the art would be able to choose the appropriate type of cross-linking agent accordingly.

Cross-linking induced by cross-linking agents may be used to vary the degradation time of the hydrogel used for the composite of the present invention. The final degradation rate of hydrogel may be measured using techniques known in the art. Most commonly, the degradation rate of a hydrogel is determined by measuring dry weight loss of the hydrogel over time.

In various embodiments, the hydrogel comprises or consists of one or more synthetic or natural hydrophilic polymers. For example, the hydrogel may comprise or consist of one or more materials selected from the group consisting of polysaccharides, proteins, polyethylene glycol, polylactic acid, polycaprolactone, polyglycolide, and combinations thereof. In some embodiments, the hydrogel comprises or consists of one or more compounds selected from the group consisting of dextran, chitosan, hyaluronic acid, gelatin, dextran dialdehyde-crosslinked gelatin, collagen, aminated hyaluronic acid, hyaluronic acid-g-poly(N-isopropylacrylamide), chitosan-hyaluronic acid, laminin, elastin, alginate, fibronectin, polyethylene glycol-fibrinogen, and derivatives thereof.

Either one of or both the hydrogel and the plurality of fibers may comprise or consist of a biodegradable polymer. The term "biodegradable" refers to a substance which may be broken down by microorganisms, or which spontaneously breaks down over a relatively short time (within 2-15 months) when exposed to environmental conditions commonly found in nature. For example, gelatin may be degraded by enzymes which are present in the body.

Examples of biodegradable polymers include, but are not limited to, polymers and oligomers of glycolide, lactide, polylactic acid, polyesters of a-hydroxy acids, including lactic acid and glycolic acid, such as the poly(a-hydroxy) acids including polyglycolic acid, poly-DL-lactic, poly-L-lactic acid, and terpolymers of DL-lactide and glycolide; e-caprolactone and e-caprolactone copolymerized with polyesters; polylactones and polycaprolactones including poly(e-caprolactone), poly(8-valerolactone) and poly (gamma-butyrolactone); polyanhydrides; polyorthoesters; other hydroxy acids; polydioxanone; and other biologically degradable polymers that are non-toxic or are present as metabolites in the body. Examples of polyaminoacids include, but are not limited to, polylysine (PLL), poly L-aspartic acid, poly L-glutamic acid, and styrene-maleic acid anhydride copolymer. Examples of derivatives of polyethylene glycol includes, but are not limited to, poly(ethylene glycol)-di-(ethylphosphatidyl(ethylene glycol)) (PEDGA), poly(ethylene glycol)-co-anhydride, poly(ethylene glycol)co-lactide, poly(ethylene glycol)-co-glycolide and poly (ethylene glycol)-co-orthoester. Examples of acrylamide polymers include, but are not limited to, polyisopropylacrylamide, and polyacrylamide. Examples of acrylate polymers include, but are not limited to, diacrylates such as polyethylene glycol diacrylate (PEGDA), oligoacrylates, methacrylates, dimethacrylates, oligomethoacrylates and PEG-oligoglycolylacrylates. Examples of carboxy alkyl cellulose include, but are not limited to, carboxymethyl cellulose and partially oxidized cellulose.

Degradation of the fiber-reinforced hydrogel composite may take place over a time period ranging from a few seconds to a few days or months. The time period required for the fiber-reinforced hydrogel composite to degrade may be dependent on a few parameters, for example, constituent of the fiber-reinforced hydrogel composite, such as type of hydrogel and/or fibers used and water content of the hydrogel, degree of cross-linking, temperature, pH, amount of aqueous medium present, and pressure during gelation. Under physiological conditions, that means in an animal body, degradation takes place over about 2 months in general. This period may be extended by varying the degree of cross-linking as described above.

In various embodiments, the hydrogel comprises or consists of dextran dialdehyde-crosslinked gelatin, in which gelatin is used as the hydrogel precursor and dextran dialdehyde is used as the cross-linking agent. The term "gelatin" as used herein refers to protein substances derived from collagen. In the context of the present invention, "gelatin" also refers to equivalent substances such as synthetic analogues of gelatin. Generally, gelatin may be classified as alkaline gelatin, acidic gelatin, or enzymatic gelatin. Alkaline gelatin may be obtained from the treatment of collagen with a base such as sodium chloride. Acidic gelatin may be obtained from the treatment of collagen with an acid such as hydrochloric acid. Enzymatic gelatin may be obtained from the treatment of collagen with an enzyme such as hydrolase. As gelatin may be a form of hydrogel, factors that affect degradation behavior of hydrogels as mentioned herein may apply to gelatin as well.

In some embodiments, the material of the hydrogel and the material of the fibers are the same. In such embodiments, the material of the hydrogel and the material of the fibers are selected such that the physical properties of the respective material are different. For example, the hydrogel material and the fiber material comprised in the fibrous component may have different elasticity and toughness.

In alternative embodiments, the material of the hydrogel and the material of the fibers are different. For example, in one specific embodiment, the composite comprises or consists of a hydrogel of dextran dialdehyde-crosslinked gelatin and fibers of bovine serum albumin.

In various embodiments, the composite comprises a plurality of layers of the hydrogel and/or a plurality of layers of the fibrous component. In other words, the composite may comprise a plurality of layers of the hydrogel and a layer of the fibrous component, or vice versa. Each of the plurality of layers of the hydrogel and/or the plurality of layers of the fibrous component may be the same or different, in terms of the thickness of the layers or the content of the layers. For example, the composite may comprise more than one layer of the hydrogel, or more than one layer of the fibrous component, or more than one layer of each of the hydrogel and fibrous component. In such embodiments, the composite may consist of alternating layers of the hydrogel and the fibrous component.

In alternate embodiments, the fibrous component comprising a plurality of fibers is at least substantially uniformly or is uniformly dispersed within the hydrogel. As mentioned previously, the composite may comprise a plurality of layers of the hydrogel and/or a plurality of layers of the fibrous component. To disperse the plurality of fibers at least substantially uniformly within the hydrogel, instead of forming the composite as a plurality of layers of the hydrogel and/or a plurality of layers of the fibrous component, the composite may be formed by first forming a layer of a hydrogel precursor film, followed by deposition of the plurality of fibers onto the hydrogel precursor film. The hydrogel precursor film containing the plurality of fibers deposited thereon may be subjected to a heat treatment to melt the hydrogel precursor film, to form a hydrogel precursor solution containing the plurality of fibers dispersed therein. To form the hydrogel, a cross-linking agent may be added to the hydrogel precursor solution, so as to cross-link the hydrogel precursor to form the hydrogel.

In embodiments wherein the plurality of fibers is formed by electrospinning, concentration of fibers inside the fiber-reinforced hydrogel composite may be controlled by controlling the duration of fiber collection, for example, from the electrospinning process, or by controlling thickness of the hydrogel layers.

In a second aspect, the present invention relates to a method of preparing a fiber reinforced hydrogel composite according to the first aspect. The method comprises coating a hydrogel precursor solution on a substrate to form a hydrogel precursor film; depositing the plurality of fibers onto the hydrogel precursor film; and allowing the hydrogel precursor film to form a hydrogel film, thereby forming the fiber-reinforced hydrogel composite.

In various embodiments, the plurality of fibers is formed by electrospinning a spinning solution containing the materials constituting the fibers. As mentioned above, it has been surprisingly found by the inventors of the present invention that use of a solution that does not contain water, for example, a non-aqueous solution, or a solution that is essentially free of water as the spinning solution, results in short-length fibers with each fiber having a length of less than about 1,000 μm, and which may be used to form the composite according to the first aspect. Accordingly, in various embodiments, the spinning solution is prepared in the absence of water.

The method of the second aspect includes coating a hydrogel precursor solution on a substrate to form a hydrogel precursor film. Depending on the type of hydrogel precursor solution used, any suitable coating or deposition methods such as spin coating, painting, or casting may be used.

The method of the second aspect includes depositing the plurality of fibers onto the hydrogel precursor film, and allowing the hydrogel precursor film to form a hydrogel film, thereby forming the fiber-reinforced hydrogel composite. The above-mentioned coating or deposition steps may take place in any suitable order, and/or take place repeatedly depending on the number of layers of the hydrogel film and/or fibrous component required. In various embodiments, a second hydrogel precursor film is deposited on the plurality of fibers, such that the plurality of fibers is sandwiched between two hydrogel precursor films.

The method of the second aspect may further comprise a heat treatment to melt the hydrogel precursor film having the plurality of fibers deposited thereon to form a hydrogel precursor solution. The heat treatment may be carried out at any suitable temperature that melts the hydrogel precursor film into its liquid form. In various embodiments in which the hydrogel precursor comprises or consists of gelatin and the plurality of fibers comprises or consists of bovine serum albumin, for example, a suitable temperature may be about 50° C. In so doing, the fibers which are deposited on the hydrogel precursor film may be dispersed at least substantially uniformly within the hydrogel precursor. To facilitate melting of the hydrogel precursor, the hydrogel precursor film having the plurality of fibers deposited thereon may be sliced, cut, or diced into smaller dimensions prior to the heat treatment. Any suitable temperature that is able to melt the hydrogel precursor may be used.

The method of the second aspect may further comprise contacting the hydrogel precursor solution having the plurality of fibers dispersed therein with a cross-linking agent to form the hydrogel. In various embodiments, gelation of the hydrogel precursor takes place such that the plurality of fibers is embedded within the hydrogel so formed. The contacting may be carried out at any suitable temperature, which may depend on the type of hydrogel precursor solution and the cross-linking agent used. For example, the cross-linking may be carried out under room temperature and pressure. In embodiments in which gelatin is used as the hydrogel precursor and dextran dialdehyde is used as the cross-linking agent for example, cross-linking may be carried out at a temperature of about 37° C. to form the fiber-reinforced hydrogel composite.

In a third aspect, the invention relates to a scaffold comprising the fiber reinforced hydrogel composite according to the first aspect. As used herein, the term "scaffold" refers to an artificial, three-dimensional structure that may be used in vivo as a framework to which additional cells may attach, and to which both existing and additional cells may grow to regenerate tissues, which may be lost through injury or disease. In various embodiments, the scaffold may be formed by pouring or injecting the composite into a mold having a desired anatomical shape, and then hardened to form the scaffold for transplant into a patient. In some embodiments, the composite is adapted to be deliverable to a site, such as a defect site, in an animal or a human body, such that the composite may be injected directly into the site in a patient to form the scaffold in vivo. The scaffold may be used as cell carriers or for placement in the body for regeneration of soft, yet load-bearing tissues (for example, but not limited to, heart muscle, cartilage and dermis).

In a fourth aspect, the present invention relates to a tissue repair method, comprising contacting the tissue with a scaffold according to the third aspect.

The term "tissue" refers to a structure formed by related cells joined together, wherein the cells work together to accomplish specific functions. In various embodiments, contacting the tissue comprises implanting the scaffold into a subject in need thereof. The term "subject" as used herein refers to any living animal, preferably a mammal, and more preferably a human. The scaffold as described herein is suitable for implantation within a subject in need thereof. In various embodiments, the scaffold may comprise cell growth media contained embryonic stem cells derived conditioned medium, which typically provides necessary nutrients and environmental conditions for cell growth. The cells may be introduced and incubated under conditions suitable for cell growth by introducing the scaffold into a patient and allowing native cells, such as stem cells to migrate into the scaffold. The scaffold may be administered by injecting the composite with embryonic stem cells derived conditioned medium into the region requiring cellular growth or remodeling, such as a region of damaged tissue or a defect site.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. By "about" in relation to a given numerical value, such as for temperature and period of time, it is meant to include numerical values within 10% of the specified value.

The invention illustratively described herein may suitably be practiced in the absence of any element or elements, limitation or limitations, not specifically disclosed herein. Thus, for example, the terms "comprising", "including", "containing", etc. shall be read expansively and without limitation. By "comprising" it is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Exemplary embodiments as shown below refer to a hybrid material containing a hydrogel of dextran dialdehyde-cross-linked gelatin, which was embedded with electrospun bovine serum albumin fibers. In the embodiments, the length of each fiber used ranged from about 100 µm to about 1000 µm. Incorporation of fibers at, for example, weight fractions of about 1% to about 6% increased the hydrogel elastic modulus by about 40%, and decreased the gelation time by about 20%.

A hybrid scaffold comprising hydrogel and short electrospun fibers is also presented. Dextran dialdehyde-crosslinked gelatin was used as the hydrogel component, and serum albumin-derived electrospun fibers having a length in the range of about 100 μm to about 1000 μm were embedded therein. FIG. 1 shows a schematic diagram of the tested hybrid biomaterial having (i) gelatin, (ii) dextran, (iii) albumin, and (iv) cells according to an embodiment. The inset shows the covalent bond between the aldehyde group of modified dextran and the amino group of gelatin. The fibers provide structural reinforcement, while the hydrogel is expected to provide a tunable matrix. The resulting scaffold may mimic common tissue ECMs at the level of both polysaccharide- and proteoglycan-based molecular networks (hydrogels) and micro-/submicro-networks, which contain protein fibers such as collagen and elastin.

Example 1: Materials

Gelatin (type A, from porcine skin), dextran (70 kDa, from *Leuconostoc* spp.), sodium periodate (ACS reagent, purity greater than 99.8%), sodium tetraborate decahydrate (Borax) and 2,2,2-trifluoroethanol (TFE, Reagent Plus®) were purchased from Sigma-Aldrich (St. Louis, Mo., USA). Bovine serum albumin (BSA, Fraction V) was purchased from MP Biomedicals (Solon, Ohio, USA). 2-mercaptoethanol (Me., molecular biology grade) was purchased from Merck (Darmstadt, Germany). All chemicals were used without further modification.

Example 2: Preparation of Composite Hydrogels

Example 2.1: Gelatin Solutions

Gelatin was dissolved in water or phosphate-buffered saline (PBS) at 50° C. to form solutions of different (w/w) concentration. Solutions were stored at 4° C. and heated to 50° C. before each experiment.

Example 2.2: Synthesis of Dextran Dialdehyde (DDA)

Dextran was dissolved in distilled water to form a 10 wt % solution, which contained 68 mmol of glucose. Three equivalents of sodium periodate dissolved in distilled water were then added in a drop-wise manner. The oxidation reaction was carried out in a dark room at room temperature for 24 h. The reddish solution was then poured into ethanol, to precipitate the resulting dextran dialdehyde (DDA). The yellowish sediment was then washed a few times in ethanol and finally in an ethanol-distilled water solution (approximately 9:1 (v/v) in ratio) to remove iodate and un-reacted salts. The resulting material was dried in vacuum for 24 h and ground into a fine powder, using a mortar and pestle.

DDA was then dissolved in Borax solutions that are either water- or PBS-based to form solutions of varying DDA (w/w) concentrations and Borax molar concentrations. Solutions were stored at 4° C. and equilibrated to 37° C. before each experiment.

Example 2.3: Fabrication of Electrospun Fibers

BSA was dissolved in TFE to form a 10 wt % BSA solution. ME was then added (0.2 g ME per 1 g of BSA) to reduce the disulfide bonds in the protein. Electrospinning was conducted at room temperature using a vertical setup that included a syringe pump (Harvard Apparatus, Holliston, Mass., USA), a 23-Gauge needle (inner diameter about 0.37 mm) and a custom-built high-voltage DC supply (30 kV max). Solution flow rate was 2 ml/hr under a voltage supply of 11 kV and a tip-to-collector distance of 15 cm.

Example 2.4: Dispersion of Albumin Fibers in Gelatin

The gelatin precursor solution was spread over a glass slide at room temperature to form a film. BSA electrospun fibers were collected and held on the film, before an additional gelatin layer was casted over them. The process was repeated to form three layers of fibers enclosed between four layers of gelatin. The layered gel was stored at 4° C. for 1 hour before being sliced into small squares, which were then melted at 50° C., to form a solution. The concentration of the fibers inside the gelatin solution was controlled by the duration of fiber collection and the thickness of gelatin layers. Fiber nominal concentration was evaluated by the difference in weight between gelatin/fiber solutions and equal volumes of gelatin. This concentration was later reduced when gelatin was mixed with the DDA precursor solution.

Three dispersions were prepared to bear low-content (L), medium-content (M) and high content (H), where L- and M-dispersion contained about 2.80% and about 5.86% nominal fiber concentration, respectively. The H-dispersion was substantially concentrated to evaluate its content and was estimated to contain about 12% nominal fiber concentration.

Example 2.5: Hydrogel Preparation

Gelatin or the gelatin/BSA fiber solution was mixed with DDA solutions at either 1:1 or 2:1 volume ratios. The resulting solutions were placed in 37° C., to allow for crosslinking within the composite hydrogel (following Schiffs base reaction).

Example 3: Microscopic Characterization

Electrospun fibers were collected on a carbon tape-covered metal stub and analyzed using Phenom desktop (5 kV accelerating voltage, FEI Company, Hillsboro, Oreg., USA) and Ultra Plus (Gemini column, 1 kV accelerating voltage, Zeiss, Oberkochen, Germany) scanning electron microscopes, as well as with an optical microscope (Olympus BX-51, Tokyo, Japan).

Example 4: Infrared Spectroscopic Measurement

Thin films of gelatin, DDA and gelatin-dextran were prepared by pouring the polymer solutions into a Teflon mold and allowing them to dry at 55° C. for three days. Fourier transform infrared (FTIR) measurements were conducted using a FTIR spectrometer (Nicolet 380, Thermo Scientific, Waltham, Mass., USA) equipped with a deuterated triglycine sulfate (DTGS) KBr detector. Each spectrum was constructed from an average of 32 scans.

Example 5: Shear Rheometry

Rheological shear measurements of the electrospun solution were conducted using a strain controlled rotational rheometer (ARES, Rheometric Scientific), with a stainless steel cone-and-plate geometry, at 25° C. Strain sweep tests were conducted to determine the linear viscoelastic regime for frequency sweep tests, and step rate (transient) tests were conducted to determine the steady state conditions for rate sweep (flow curve) tests.

Rheological shear measurements of the precursor solutions and hydrogels were conducted using a strain controlled rotational rheometer (AR-G2, TA Instruments, New Castle, Del., USA), with a stainless steel parallel plate geometry (20 mm), which included a Peltier temperature control. All tests were conducted at 37° C. Evaporation of water was prevented using the solvent trap provided with the rheometer. Various precursor solutions, gelatin-DDA mixing ratios, and final Borax concentrations were tested. The precursor gelatin solutions were stored at 50° C., mixed with DDA solutions and immediately injected (about 350 μl) onto the bottom plate of the rheometer. The upper plate was set down at a distance of 950 μm. A time sweep test was conducted within 2 min of solution mixing, at a frequency of 1 s$^{-1}$ and strain amplitude of 3%, in order to evaluate the gelation point. At the end of the time sweep test, a strain sweep test was conducted at 1 s$^{-1}$ to determine the linear viscoelastic regime of the hydrogels. Flow curve tests were performed on pre-gel solutions, using the steady state averaging tool of the rheometer operating software.

Example 6: Biocompatibility Testing

Normal human dermal fibroblasts (NHDF) (Lonza, Basel, Switzerland) were cultured in Dulbecco's Modified Eagle's Medium (DMEM) (Gibco, Paisley, UK) supplemented with 10% fetal bovine serum (FBS) (Hyclone, Cramlington, UK), 1% penicillin/streptomycin antibiotics (Biological Industries, Beit-Haemek, Israel), 1% non-essential amino acid solution (NEAA) (Biological Industries), and 0.2% ME (Sigma-Aldrich). Sterilization of DDA precursor solutions was done using a 0.22 μm syringe filter, whereas gelatin precursor solutions were UV-treated for 20 min. Cells were suspended in DDA and then mixed with gelatin to form 0.5 ml hydrogel samples. The final seeding density was 1×10$^6$ cells/ml. Cell-embedded hydrogels were then incubated for 1 hour at 37° C. to allow for chemical crosslinking before addition of media. Culture media were replaced three times during the one-week culture period. Images were taken during the culture period using an Eclipse TS100 inverted microscope (Nikon Instruments, Melville, N.Y., USA). Viability assays were conducted using calcein AM (cytoplasmic marker) and ethidium homodimer-1 (nucleic acids dye) (Sigma-Aldrich), according to standard protocols. Images of cells within the whole constructs were taken using a super-zoom macro-confocal microscope (Leica TCS LSI, Wetzlar, Germany).

Example 7: Chemical Structure of Gelatin-Dextran Hydrogels

Figure 2:
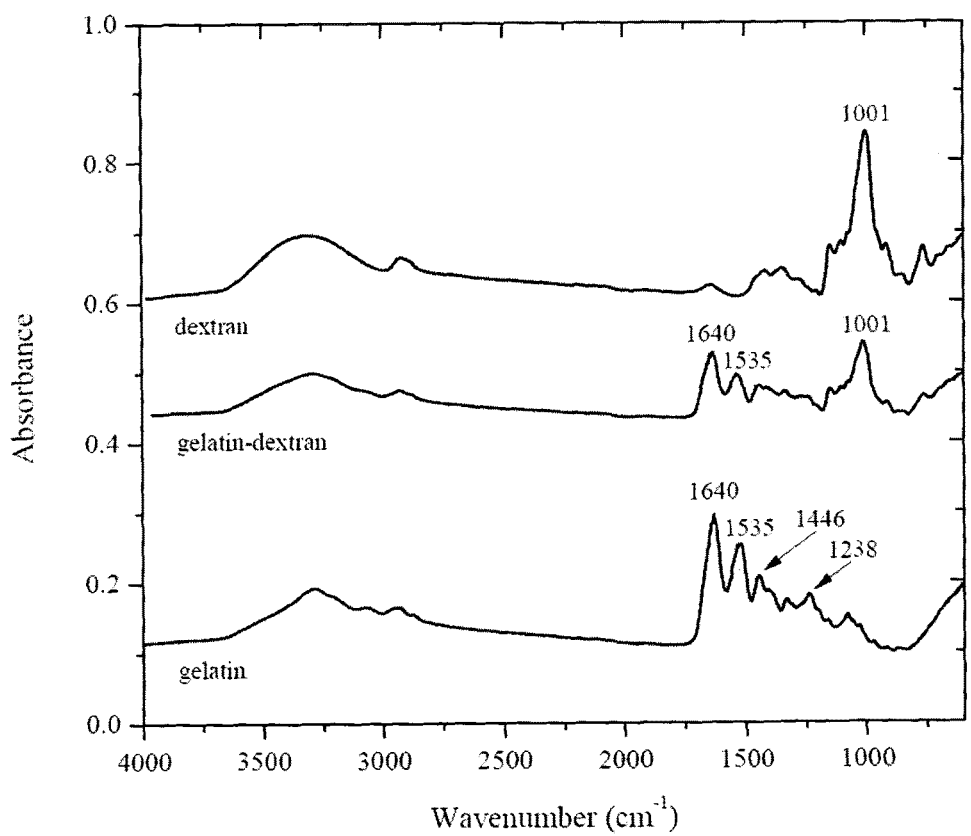
FIG. 2 is a graph showing Fourier Transform Infra-red (FTIR) spectroscopy spectra of gelatin, dextran dialdehyde and crosslinked gelatin-dextran.

The FTIR spectra of gelatin, DDA and DDA-crosslinked gelatin (gelatin-dextran) were collected and shown in FIG. 2. The gelatin spectrum was characterized by two strong peaks at about 1535 cm$^{-1}$ and 1640 cm$^{-1}$, attributed to C—N and C=O stretching vibrations, respectively, in secondary amides that connect the amino acid monomers. The DDA spectrum was characterized by a strong peak at about 1000 cm$^{-1}$ that is attributed to the C—O stretching vibrations at the ether linkage of the glucose monomers. These three peaks were also the primary peaks in the gelatin-dextran spectrum, as expected even following simple blending.

The Schiffs base reaction between amines (in the gelatin) and between aldehydes (in the modified dextran) results in imine groups that contain a carbon-nitrogen double bond. The C=N stretching vibrations are typically characterized by a medium peak at 1620 cm$^{-1}$ to 1650 cm$^{-1}$ which may have been masked by peaks of the vibrations in the secondary amides along the gelatin chain. In addition, two medium-sized peaks at 1238 cm$^{-1}$ and 1446 cm$^{-1}$ in the gelatin spectrum, were not detected in analyses of gelatin-dextran. The former is attributed to the C—N stretching vibrations in primary amines and the latter, to the N—H bending vibrations in primary amides. These groups are found in the side chains of amino acids such as lysine, glutamine and asparagine and are potential sites for Schiffs base links. The disappearance of these peaks provides evidence for the crosslinked nature of the gelatin-dextran network.

Example 8: Morphology of Short Electrospun Fibers

In general, a stable electrospinning process results in long uniform fibers, while an unstable process, resulting from insufficient extensional viscosity of the electrospun jet, leads to formation of drops or beads-on-string structures. The correlation between the rheological properties of BSA solutions and the resulting as-spun structures, namely drops, beads-on-string fragments, or long uniform fibers, was studied by Regev et al. (O. Regev et al., Polymer 2010, 51, 2611).

Figure 3:
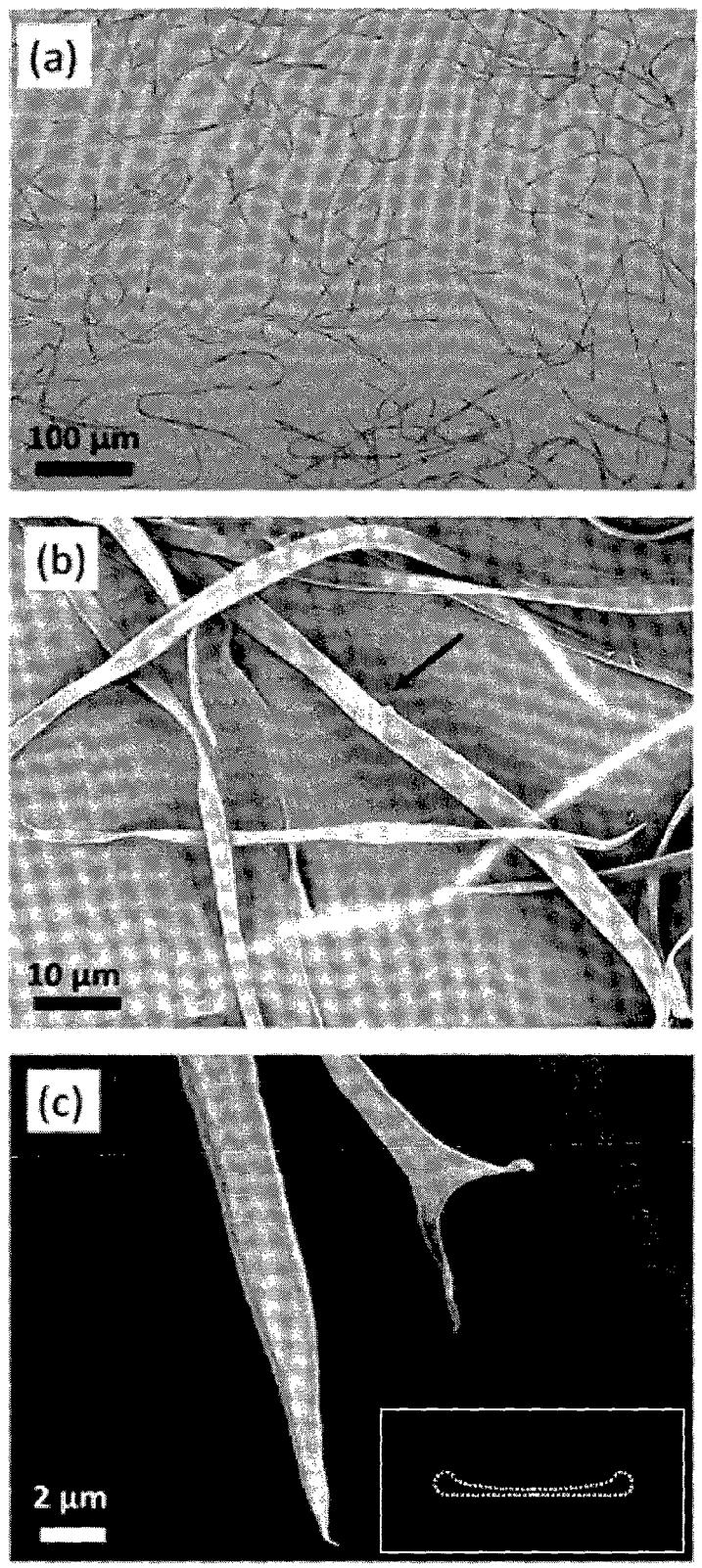
FIG. 3 shows (a) optical; (b) and (c) scanning electron microscopy (SEM) images of electrospun short fibers according to various embodiments. Referring to (b), the arrow points to a fibrillar structure. (c) depicts fractured fibers with a sharp end and bi-tails. The inset in (c) shows a sketch of the fiber cross-section. Magnification is 10,000× in (c) (Ultra Plus). The scale bar in (a), (b) and (c) denote a length of 100 µm, 10 µm, and 2 µm respectively.

FIG. 3 shows (a) optical; (b) and (c) scanning electron microscopy (SEM) images of electrospun short fibers according to various embodiments. Referring to (b), the arrow points to a fibrillar structure. (c) depicts fractured fibers with a sharp end and bi-tails. The inset in (c) shows a sketch of the fiber cross-section. Magnification is 10,000× in (c) (Ultra Plus).

The spinning solution in the current study, which produced 100 μm to 1000 μm-long fibers such as that shown in FIG. 3(a), differed from that which yields long fibers in that it did not include water. Its bulk shear viscosity, 1.43 Pa·s, is higher than that of long fiber-yielding spinning solutions (0.35 Pa·s, see Regev et al.), indicating that the volume occupied by the protein chain in the present solution is higher. This observation lies in agreement with the known effect of TFE on protein conformation in solution. Namely, at high TFE concentrations, the molecules are stabilized in an open-helical structure, where the favored secondary structure is α-helix and the tertiary structure tends to an unfolded state. Therefore, the present protein solution was expected to be more stable during the spinning process due to its high extensional viscosity along the electrospun jet. However, its electrospinning generated a unique structure of short uniform fibers. High magnification images of the as-spun fibers as shown in FIGS. 3(b) and (c) expose a ribbon-like shape likely resulting from fiber collapse (radial buckling), consequential of entrapped solvent and rapid evaporation of the highly volatile TFE, which takes place during electrospinning. The fibers can be characterized by their ductile sharp ends or by the more prevalent bi-tails with thick edges that facilitate high elongation as shown in FIG. 3(c). These bi-tails are thought to have formed as a result of the inhomogeneous cross-sectioning of the fiber (see inset in FIG. 3(c)).

From the results obtained, it is hypothesized that water molecules in electrospinning solutions may act as plasticizers to reduce the cohesive intermolecular interaction, and result in a more ductile solution, thereby allowing the spinning thread to stretch without jet breakage. It follows that the absence of water in the present electrospun solution resulted in a more brittle material, which may also affect the occurrence of instabilities in the stretched dry jet.

Example 9: Mechanical Characterization of Hydrogel/Electrospun Fiber Composites

The mechanical properties of gelatin-dextran hydrogels have been previously studied under various production conditions, including ranges of temperature during gelation, pH, oxidation level of dextran, molecular weight of polymers and gelatin/dextran weight ratios.

Aqueous solutions of gelatin form a physical gel below the sol-gel transition temperature (about 40° C.). In the present experiments, pre-heated precursor solutions were mixed and then immediately injected onto the rheometer plates, thus assuring minimal formation of physical crosslinks between the gelatin chains. The resulting gel is therefore 'locked' by the chemical crosslinks between gelatin and dextran chains, and contribution of physical crosslinking is minimal. This assures stable gel properties during both handling and environmental changes.

In situ gelation of the pre-gel solution allows for determination of the gelation point, and assures that the hydrogel is well attached to the plates, essential when performing tests involving large strain amplitudes.

In oscillatory shear tests, the storage modulus G' and loss modulus G" are evaluated.

The inverse tangent of G"/G', the phase angle δ, describes the material as either a viscous-like liquid (solution) or an elastic-like solid (gel). The lower the phase angle, the higher the elastic property (G') relative to the viscous property (G") of a material. The material closely resembles a gel phase (see insets in FIG. 4). The time to crossing of the G' and G" curves, δ=45°, is typically regarded as the gelation point. The following data regard the tested hydrogel without fibers (control) and with three fiber concentrations, namely low-content (L), medium-content (M) and high-content (H) composites, containing about 1.4%, about 2.9% and about 6% nominal fiber weight concentration, respectively.

Figure 4:
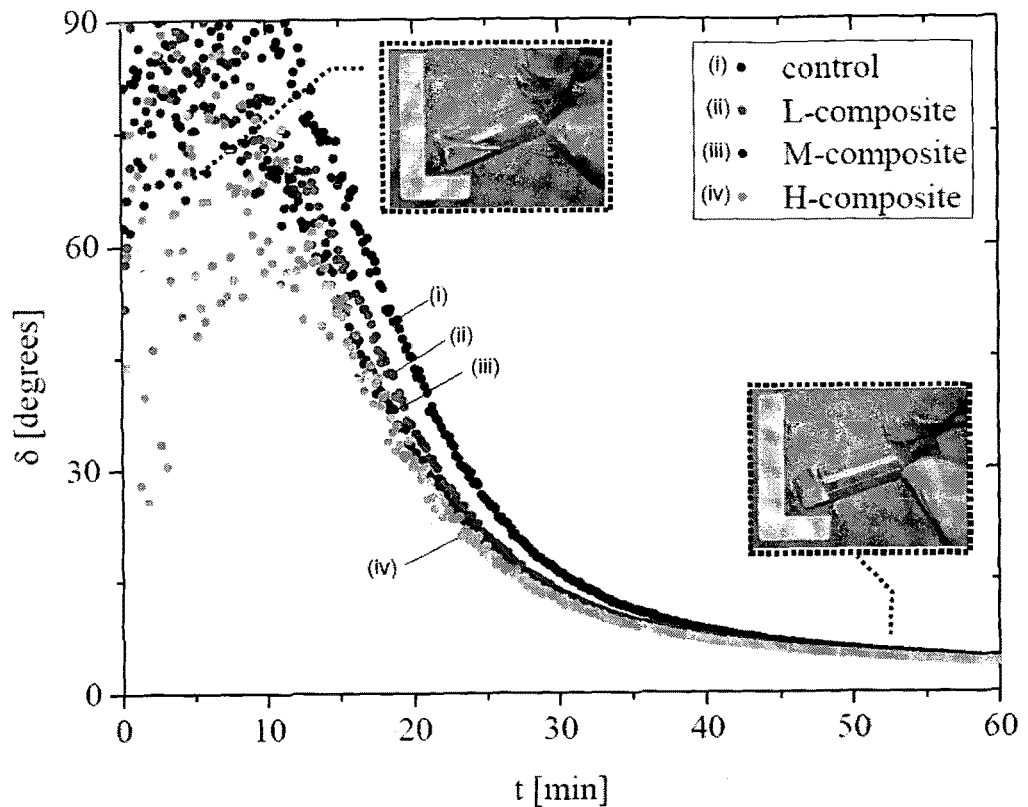
FIG. 4 is a graph showing results from time sweep experiments carried out on the tested hydrogels of (i) control, (ii) L-composite, (iii) M-composite, and (iv) H-composite. Phase angle $\delta = \tan^{-1}(G''/G')$, is plotted vs. time. Tested hydrogels were prepared by mixing 10 wt % polymer precursor solutions in a 1:1 ratio. L, M and H denote nominal fiber weight contents of about 1.4%, about 2.9%, and about 6% respectively. Frequency was 1 s$^{-1}$ and strain 3%. The insets show optical images of pre-gel solution (left image) and gel (right image).

FIG. 4 is a graph showing results from time sweep experiments carried out on the tested hydrogels of (i) control, (ii) L-composite, (iii) M-composite, and (iv) H-composite. Phase angle δ=tan$^{-1}$ (G"/G'), is plotted vs. time. Tested hydrogels were prepared by mixing 10 wt % polymer precursor solutions in a 1:1 ratio. L, M and H denote nominal fiber weight contents of about 1.4%, about 2.9%, and about 6% respectively. Frequency was 1 s$^{-1}$ and strain 3%. The insets show optical images of pre-gel solution (left image) and gel (right image).

Figure 5:
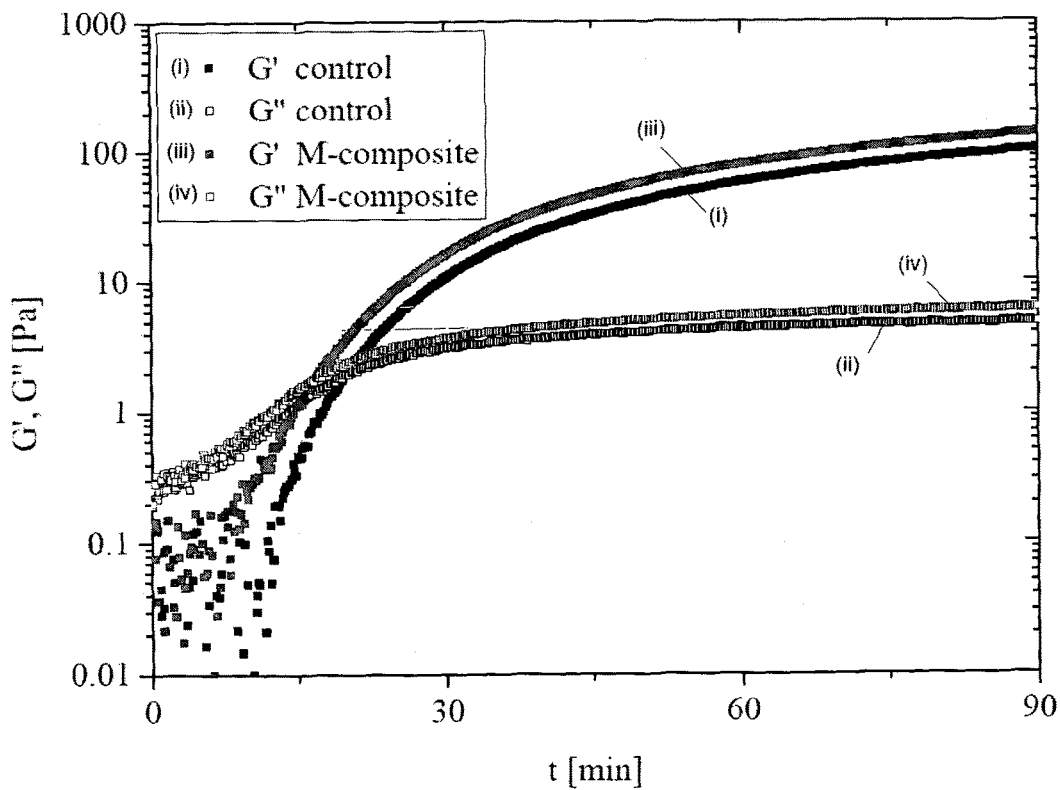
FIG. 5 is a graph showing results from time sweep experiments carried out on the tested hydrogels of (i) G' control, (ii) G'' control, (iii) G' M-composite, and (iv) G'' M-composite. Storage G' (full symbols) and loss G'' (open symbols) moduli are plotted vs. time. M denotes nominal fiber weight content of about 2.9%. Frequency was 1 s$^{-1}$ and strain 3%.

FIG. 5 is a graph showing results from time sweep experiments carried out on the tested hydrogels of (i) G' control, (ii) G" control, (iii) G' M-composite, and (iv) G" M-composite. Storage G' (full symbols) and loss G" (open symbols) moduli are plotted vs. time. M denotes nominal fiber weight content of about 2.9%. Frequency was 1 s$^{-1}$ and strain 3%.

Time sweep experiments of hydrogels prepared from a solution of 10 wt % gelatin in water (with or without BSA fibers) mixed 1:1 with a solution of 10 wt % DDA and 0.01 M Borax in water, demonstrated that gelation occurred at a faster rate as fiber concentration increased (see FIG. 4), and resulted in composites with a higher elastic modulus (fiber reinforcement) (see FIG. 5). The control sample gelled within 20 min and reached G' of 100 Pa after 90 min, whereas the three composites gelled within 16 min to 17.5 min and reached G' of 135 Pa to 140 Pa. These findings suggest that amine groups of albumin fibers form Schiff's base links with the aldehyde groups of modified dextran chains (see FIG. 1). Interestingly, hydrogels prepared from a solution of 10% gelatin mixed 2:1 with a solution of 10% DDA and 0.02 M Borax, demonstrated different trends. The storage modulus of these hybrids was higher than that of the control, but the time-to-gelation was similar and even longer for hybrids (data not shown). During the first minutes of gelation, the phase angle of these hybrids was lower than that of the control, but then became higher during the gel-forming period, and eventually reached similar values. These differences show how the concentration of polymers and Borax and their relative ratios in the resulting hydrogel, affect the gelation process in the presence of fibers as well as the extent of reinforcement.

In order to further explore the albumin-dextran interaction, FTIR measurements were conducted on dry short BSA fiber mats that were immersed in a DDA Borax solution for 1 hour. After washing for 1 hour in PBS, a strong peak was observable at about 1000 cm$^{-1}$ (ether linkage in dextran backbone) (data not shown). This peak, together with the typical peak of the protein at about 1640 cm$^{-1}$, was significantly reduced after further washing for 24 h in PBS. These findings hint to the instability of short fiber mats in solution, do not confirm that a covalent bond is formed between BSA and DDA chains, but do suggest a strong adhesion between the polymers, which may be of a non-covalent nature.

Figure 6:
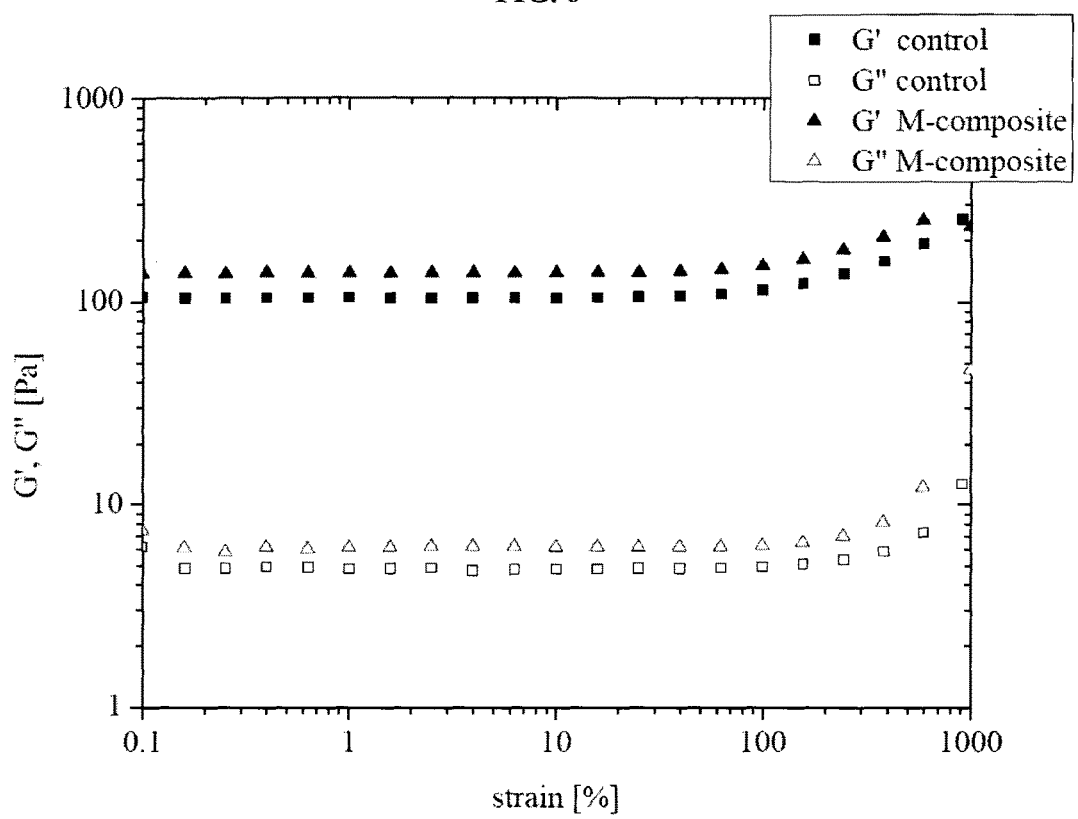
FIG. 6 is a graph showing results from strain sweep experiments of hydrogels (i) G' control (symbol: full square), (ii) G'' control (symbol: open square), (iii) G' M-composite (symbol: full triangle), and (iv) G'' M-composite (symbol: open triangle). Storage G' (full symbols) and loss G'' (open symbols) moduli are plotted vs. strain amplitude. M denotes nominal fiber weight content of about 2.9%. Frequency was 1 s$^{-1}$.

A strain sweep experiment was conducted to assess hydrogel durability under large deformations. FIG. 6 is a graph showing results from strain sweep experiments of hydrogels (i) G' control (symbol: full square), (ii) G" control (symbol: open square), (iii) G' M-composite (symbol: full triangle), and (iv) G" M-composite (symbol: open triangle). Storage G' (full symbols) and loss G" (open symbols) moduli are plotted vs. strain amplitude. M denotes nominal fiber weight content of about 2.9%. Frequency was 1 s$^{-1}$.

All tested hydrogels featured wide linear regions where the moduli were constant up to strain amplitudes of 100%. After this point, they reacted with increased moduli, suggesting non-linear viscoelasticity, until failure at approximately 1000% amplitude. It is important to note that in biological environments, hydrogels are swollen with water and salts and, as a result, the elastic modulus is expected to be somewhat smaller than that which is experimentally measured.

All tested hydrogel/fiber composites were easily injected through 21, 25 and 30-gauge hypodermic needles before the sol-gel transition occurred (data not shown). In order to evaluate the flow properties of the pre-gel solution during the first seconds of injection, a Borax-free gelatin/dextran solution (12 wt % gelatin in PBS mixed 2:1 with 10 wt % DDA in PBS) was analyzed in steady state flow experiments.

Figure 7:
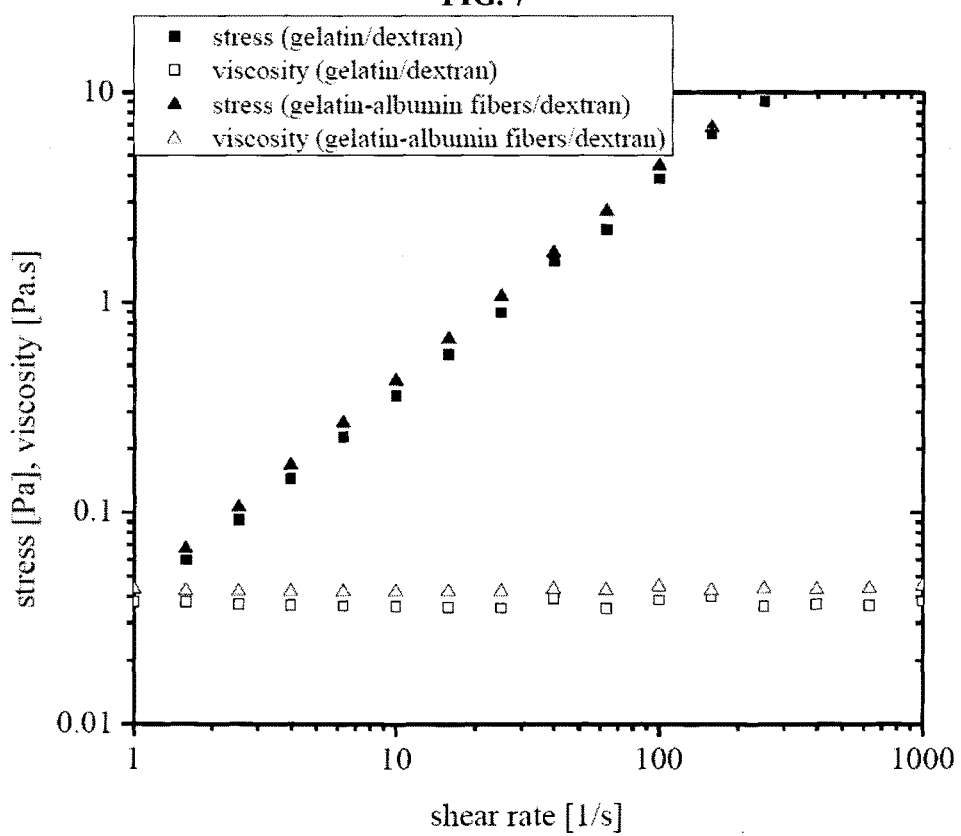
FIG. 7 is a graph showing shear rate sweep (flow) experiments of the pre-gel solutions of gelatin/dextran hydrogel (squares) and hybrid gelatin-albumin fibers/dextran composites (triangles). Each point represents an average measurement of 20 sec; waiting time for steady state was 1 min.

FIG. 7 is a graph showing shear rate sweep (flow) experiments of the pre-gel solutions of gelatin/dextran hydrogel (squares) and hybrid gelatin-albumin fibers/dextran composites (triangles). Each point represents an average measurement of 20 sec; waiting time for steady state was 1 min.

As may be seen from FIG. 7, the above solution is free of crosslinks, thereby allowing for rheological tests over unlimited time periods. The addition of short BSA fibers did not affect the Newtonian behavior of the pre-gel solution and only induced a minor increase in its shear viscosity.

Example 10: In Vitro Analysis of Injectable Hydrogel/Fiber Composites

Figure 8:
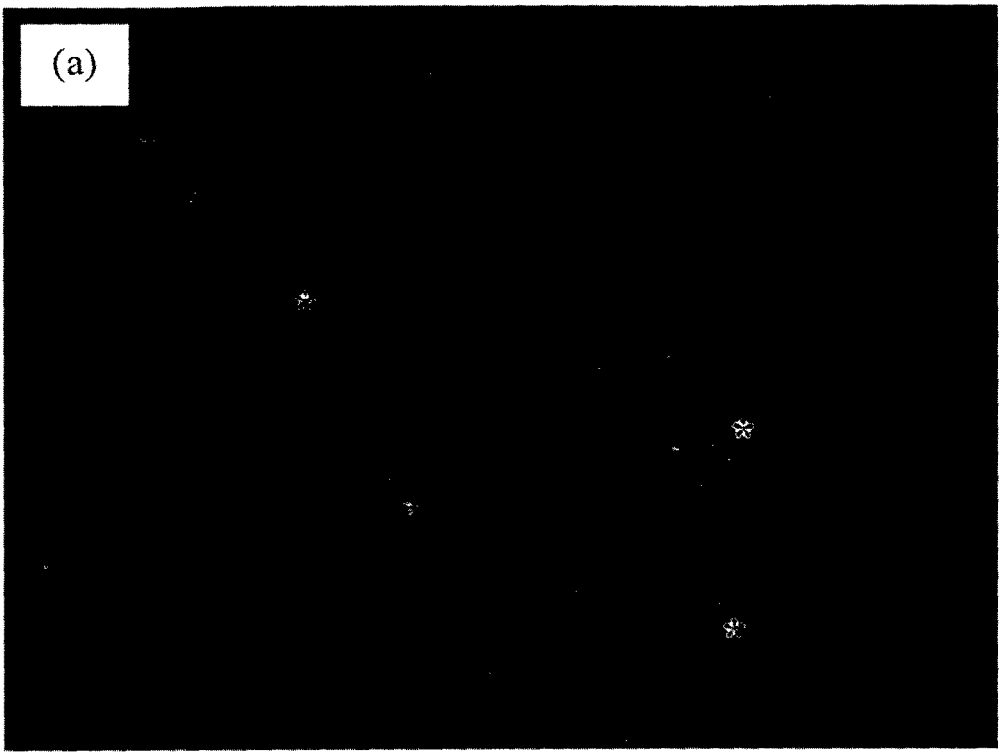
FIG. 8 depicts cell adherence on hydrogel/fiber composites. Fibroblasts (asterisks) grown in (a) Dextran Dialdehyde (DDA)-gelatin hydrogel; or (b) composite with fiber content of about 3.9% for two days. The arrow indicates a bovine serum albumin (BSA) fiber. Magnification is 100×.
Figure 8:

In vitro studies of fibroblast growth were performed in hydrogels prepared from a solution of 12% gelatin in PBS (with or without BSA fibers) mixed 2:1 with a solution of 10% DDA and 0.03 M Borax in PBS, following the mixing ratio of previous studies. Fibroblasts cultured on the hydrogels for either two or four days, adhered and grew across the hydrogel, owing apparently to recognition sequences, e.g. Arg-Gly-Asp (RGD), characteristic of collagen molecules. FIG. 8 depicts cell adherence on hydrogel/fiber composites. Fibroblasts (asterisks) grown in (a) DDA-gelatin hydrogel; or (b) composite with fiber content of about 3.9% for two days. The arrow indicates a BSA fiber. Magnification is 100×.

Figure 9:
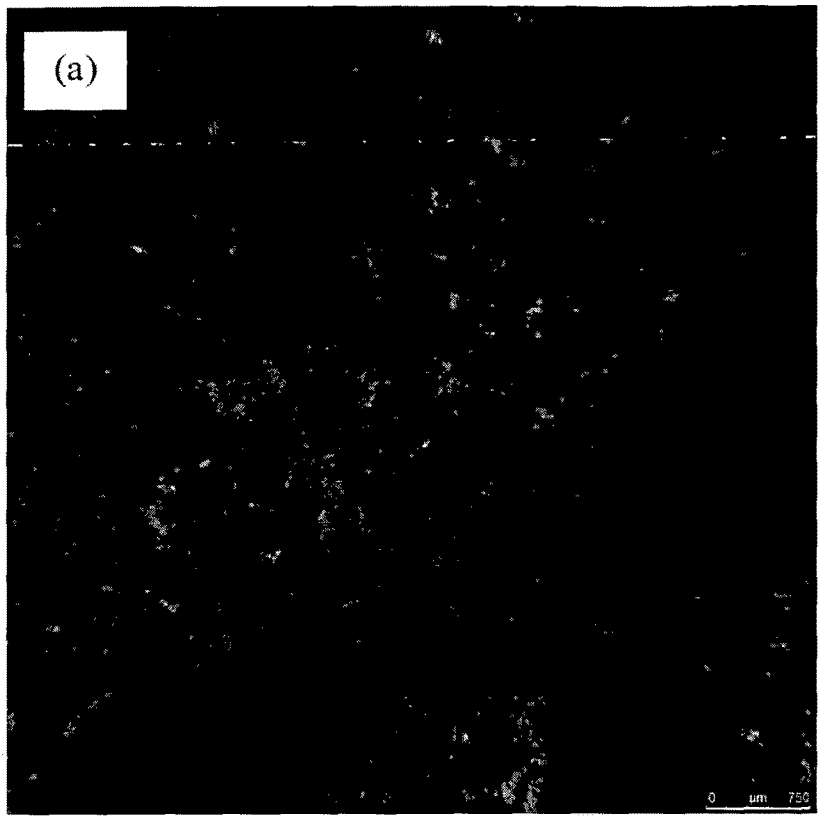
FIG. 9 depicts cell viability on hydrogel/fiber composites. Viability assays were performed on fibroblasts grown for two days in (a) DDA-gelatin hydrogel; or (b) composite with fiber content of about 3.9%. Live cells and dead cells are stained green and red respectively. The scale bar in (a) and (b) denotes a length of 750 μm.
Figure 9:
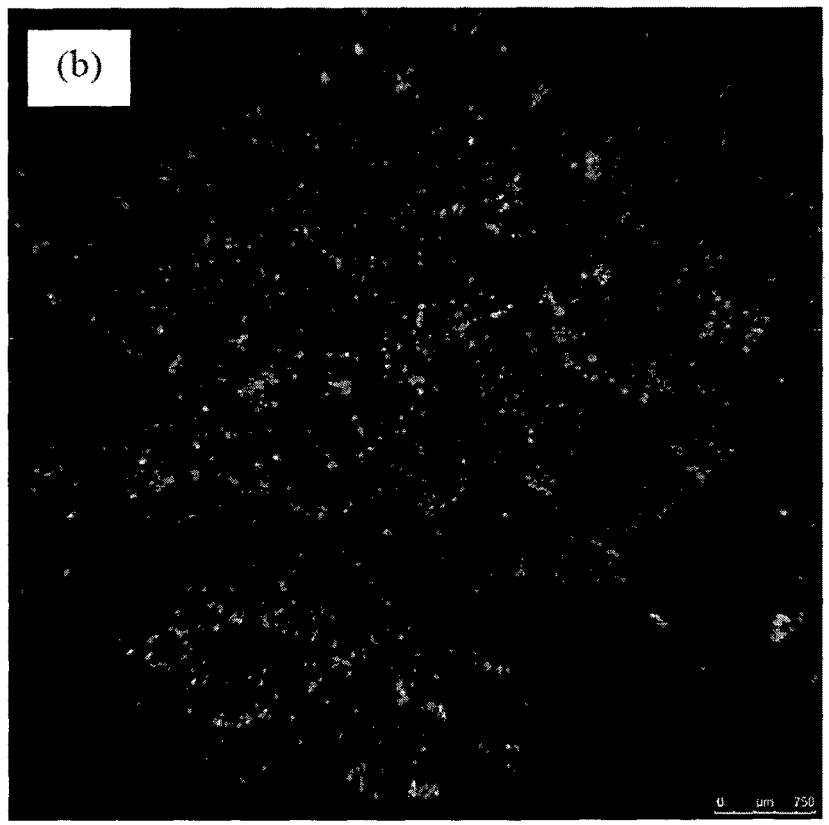

BSA fibers were non-toxic, as demonstrated by similar cell viability in both hydrogel and hybrid systems. FIG. 9 depicts cell viability on hydrogel/fiber composites. Viability assays were performed on fibroblasts grown for two days in (a) DDA-gelatin hydrogel; or (b) composite with fiber content of about 3.9%. Live cells and dead cells are stained green and red respectively. The scale bar in (a) and (b) denotes a length of 750 μm. The images in FIG. 9 are 3-D construct (Z-stack) of successive images taken in different height across the scaffold, where each cross-section image was confirmed as containing living cells (data not shown). Note the small amount of dead cells (red color) in the confocal images. Cell-embedded composites were stable for at least one week in vitro.

Few cell types, among them fibroblasts from specific origins, present albumin binding proteins (ABPs) such as gp30 and gp18. These proteins act as scavenger receptors that bind denatured serum albumin and stimulate their degradation. It is therefore expected that only specific cell types will interact with the BSA fiber surfaces. However, this interaction will only be noticeable in composites containing higher fiber concentrations than those presented here, or, alternatively, with cell types expressing higher concentrations of ABPs, such as endothelial cells.

It was previously demonstrated that cells proceed through a soft hydrogel or induce its contraction until they are signaled by a stiffer component inside the hydrogel/fiber composite material. Ghosh et al. (Ghosh et al., Biomaterials 2007, 28, 671) showed that fibroblasts migrate faster on a soft fibronectin (FN) hydrogel, but preferentially proliferate on the stiffer HA/FN hybrid hydrogel. In the present study, the immersed protein fibers are relatively soft, with a wet fiber network modulus of about 0.35 MPa (unpublished data). The local stiffness of a single fiber is expected to be even lower, i.e. between two or three orders of magnitude higher than the modulus of the tested hydrogel.

This work presents a thorough rheological analysis of the described composite, prepared with increasing concentrations of electrospun fibers, in efforts to analyze the resulting mechanical and flow properties. Biocompatibility was also evaluated by monitoring viability of fibroblasts embedded within the constructs. Conclusions of this study are generally applicable to future investigations of hybrid scaffolds made of functional highly flexible, short fiber embedded hydrogel.

A fiber-reinforced hydrogel composite comprising a hydrogel and a fibrous component comprising a plurality of fibers, wherein the length of each of the plurality of fibers is less than about 1,000 μm is provided. Exemplary embodiments describe a hybrid material composed of dextran dialdehyde-crosslinked gelatin embedded with electrospun albumin fibers with typical aspect ratio of 100:1. As may be seen from the results obtained, incorporation of albumin fibers into dextran-gelatin molecular networks improves the elastic behavior of hydrogel and reduces time to gelation. For example, the elastic behavior of the hydrogel was increased by about 40% and the time-to-gelation was reduced by about 20%, but still allowed for injection of the composite. During injection, the flow parameters of the hybrid pre-gel solution were similar to those of the hydrogel solution. In vitro studies demonstrated that fiber-enriched hydrogels are biocompatible and support fibroblast growth.

The proposed approach for preparation of hydrogel/fiber hybrid materials may result in formation of biological, chemical and mechanical surface or structural cues critical for cell migration, proliferation, and differentiation. These cues could be obtained for example by designing the hydrogel/fiber modulus mismatch, by integrating bio-recognition sequences onto fiber surface to enhance cell adhesion, or by encapsulating morphogens within the fibers and subsequently their control release.

Potential applications of these biomaterials include space-filling scaffolds and cell carriers, for the regeneration of soft, yet load-bearing tissues (e.g. heart muscle, cartilage and dermis), where the need to enhance the mechanical properties of currently available materials exists.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A fiber-reinforced hydrogel composite comprising:
a hydrogel; and
a fibrous component comprising a plurality of fibers, wherein the fibers comprise albumin, collagen, elastin, alginate, polylactide, polyamide, poly(siloxane), poly (silicone), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polyglycolide, poly (lactide-co-glycolide), polyanhydride, polyorthoester, poly(carbonate), poly(ethylene oxide), polyaniline, poly(vinyl phenol), polyhydroxyacid, poly(caprolactone), polyhydroxyalkanoate, polyurethane, chitosan, starch, hyaluronic acid, blends thereof, or copolymers thereof, and wherein the length of each of the plurality of fibers is less than about 1,000 um; wherein the fiber-reinforced hydrogel is a molded fiber-reinforced hydrogel.

2. The composite of claim 1, wherein the length of each of the plurality of fibers is about 100 μm to about 1,000 μm.

3. The composite of claim 1, wherein the plurality of fibers consists of electrospun fibers.

4. The composite of claim 1, wherein the composite consists of less than about 10 wt % of the fibrous component based on the total weight of the composite.

5. The composite of claim 4, wherein the composite consists of about 1 wt % to about 6 wt % of the fibrous component based on the total weight of the composite.

6. The composite of claim 1, comprising a plurality of layers of the hydrogel and/or a plurality of layers of the fibrous component.

7. The composite of claim 6, wherein the composite consists of alternating layers of the hydrogel and the fibrous component.

8. The composite of claim 1, wherein the fibers consist of serum albumin.

9. The composite of claim 8, wherein the fibers consist of bovine serum albumin.

10. The composite of claim 8, wherein the hydrogel comprises dextran dialdehyde-crosslinked gelatin.

11. The composite of claim 1, wherein the hydrogel comprises one or more synthetic or natural hydrophilic polymers.

12. The composite of claim 11, wherein the hydrogel comprises one or more materials selected from the group consisting of polysaccharides, proteins, polyethylene glycol, polylactic acid, polycaprolactone, polyglycolide, and combinations thereof.

13. The composite of claim 12, wherein the hydrogel comprises one or more compounds selected from the group consisting of dextran, chitosan, hyaluronic acid, gelatin, dextran dialdehyde-crosslinked gelatin, collagen, aminated hyaluronic acid, hyaluronic acid-g-poly(N-isopropylacrylamide), chitosan-hyaluronic acid, laminin, elastin, alginate, fibronectin, polyethylene glycolfibrinogen and derivatives thereof.

14. The composite of claim 13, wherein the hydrogel comprises dextran dialdehyde-crosslinked gelatin.

15. The composite of claim 1, wherein the material of the hydrogel and the material of the fibers are different.

16. A scaffold having a three-dimensional shape, comprising a fiber-reinforced hydrogel composite including: a hydrogel; and a fibrous component comprising a plurality of fibers, wherein the fibers comprise albumin, collagen, elastin, alginate, polylactide, polyamide, poly(siloxane), poly(silicone), poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), poly(vinyl acetate), polyacrylamide, poly(ethylene-co-vinyl acetate), poly(ethylene glycol), poly(methacrylic acid), polyglycolide, poly(lactide-co-glycolide), polyanhydride, polyorthoester, poly(carbonate), poly(ethylene oxide), polyaniline, poly(vinyl phenol), polyhydroxyacid, poly(caprolactone), polyhydroxyalkanoate, polyurethane, chitosan, starch, hyaluronic acid, blends thereof, or copolymers thereof, and wherein the length of each of the plurality of fibers is less than about 1,000 um; wherein the fiber-reinforced hydrogel is a molded fiber-reinforced hydrogel.

* * * * *